US00RE40095E

(19) United States
(12) Reissued Patent
Dutton

(10) Patent Number: US RE40,095 E
(45) Date of Reissued Patent: Feb. 26, 2008

(54) CORRECTION OF CORIOLIS FLOWMETER MEASUREMENTS DUE TO MULTIPHASE FLOWS

(75) Inventor: Robert E. Dutton, Louisville, CO (US)

(73) Assignee: Micro Motion, Inc., Boulder, CO (US)

(21) Appl. No.: 10/430,879

(22) Filed: May 6, 2003

(Under 37 CFR 1.47)

Related U.S. Patent Documents

Reissue of:
(64) Patent No.: 6,327,914
Issued: Dec. 11, 2001
Appl. No.: 09/163,529
Filed: Sep. 30, 1998

(51) Int. Cl.
*G01F 1/84* (2006.01)

(52) U.S. Cl. ..... 73/861.356; 73/861.357; 73/861.355

(58) Field of Classification Search ..... 73/861.356, 73/32 A, 861.357, 861.355, 861.354, 861.351, 73/861.04, 195, 198, 19.03, 61.45
See application file for complete search history.

(56) References Cited

U.S. PATENT DOCUMENTS 31,450 A * 2/1861 Fleury
4,491,025 A * 1/1985 Smith
4,872,351 A 10/1989 Ruesch
4,911,006 A * 3/1990 Hargarten et al. ..... 73/198
5,029,482 A * 7/1991 Liu
5,224,387 A 7/1993 Lindenbaum et al.
5,295,084 A * 3/1994 Arunachalam et al. ..... 73/32 A
5,555,190 A * 9/1996 Derby et al. ..... 73/861.356
5,570,300 A * 10/1996 Henry et al.
5,594,180 A * 1/1997 Carpenter et al.
5,654,502 A * 8/1997 Dutton
5,687,100 A * 11/1997 Buttler et al. ..... 73/32 A
5,804,741 A * 9/1998 Freeman ..... 73/861.356
5,823,262 A * 10/1998 Dutton ..... 166/250.15
6,092,409 A * 7/2000 Patten et al. ..... 73/1.34

FOREIGN PATENT DOCUMENTS

SU 1580171 A1 7/1990

* cited by examiner

*Primary Examiner*—Jewel Thompson
(74) *Attorney, Agent, or Firm*—The Ollila Law Group LLC

(57) ABSTRACT

A Coriolis flowmeter is operable as a vibrating tube densitometer where a flowtube is driven to vibrate at a fundamental frequency from which density of the material flowing through the flowtube may be calculated. The drive gain is monitored as an indicator of multiphase flow including gas and liquid components where a substantial increase in drive gain indicates gas damping of the flowtube vibrations due to a transient bubble entering the flowtube. The gas damping effects of the transient bubble and the correspondingly reduced density readings are remediated by the use of historical density measurements corresponding to periods of flow when no transient bubble has entered the flowtube.

70 Claims, 5 Drawing Sheets

FIG. 2
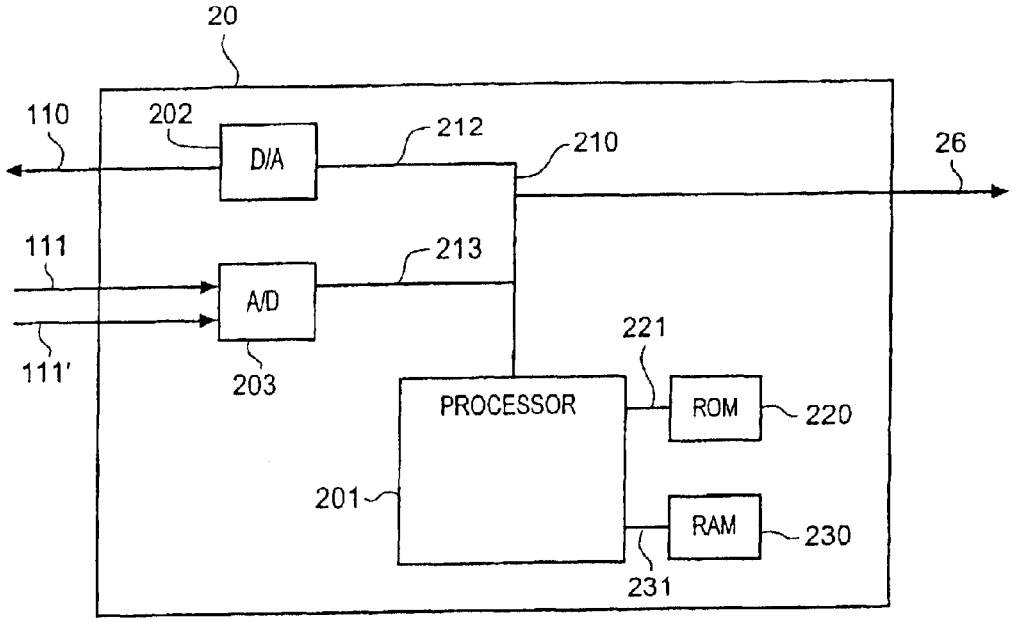
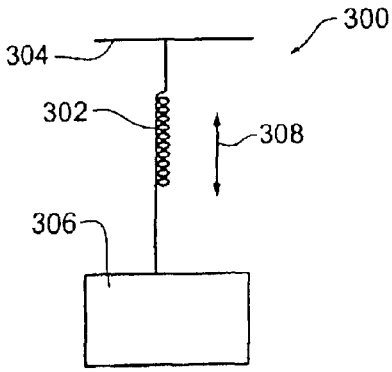
FIG. 3
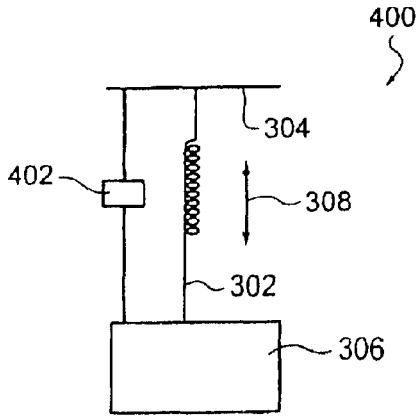
FIG. 4

CORRECTION OF CORIOLIS FLOWMETER MEASUREMENTS DUE TO MULTIPHASE FLOWS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention pertains to Coriolis effect mass flowmeters. More particularly, the Coriolis effect mass flowmeters contain self diagnostics that improve the accuracy obtainable from the meters in measuring two phase flow including mixtures of gas and liquid, or in identifying measurements that may be affected by the deposition of scale or wax inside the meter.

2. Statement of the Problem

Coriolis flowmeters directly measure the rate of mass flow through a conduit. As disclosed in the art, such as in U.S. Pat. No. 4,491,025 (issued to J. E. Smith et al. on Jan. 1, 1985 and hereinafter referred to as the U.S. Pat. No. 4,491,025) and Re. 31,450 (issued to J. E. Smith on Feb. 11, 1982 and hereinafter referred to as the U.S. Pat. No. Re. 31,450), these flowmeters have one or more flowtubes of straight or curved configuration. Each flowtube configuration in a Coriolis mass flowmeter has a set of natural vibration modes, which may be of a simple bending, torsional or coupled type. Fluid flows into the flowmeter from the adjacent pipeline on the inlet side, is directed through the flowtube or tubes, and exits the flowmeter through the outlet side of the flowmeter. The natural vibration modes of the vibrating, fluid filled system are defined in part by the combined mass of the flowtubes and the fluid within the flowtubes. Each flow conduit is driven to oscillate at resonance in one of these natural modes.

When there is no flow through the flowmeter, all points along the flowtube oscillate with identical phase. As fluid begins to flow, Coriolis accelerations cause each point along the flowtube to have a different phase. The phase on the inlet side of the flowtube lags the driver, while the phase on the outlet side leads the driver. Sensors can be placed on the flowtube to produce sinusoidal signals representative of the motion of the flowtube. The phase difference between two sensor signals is proportional to the mass flow rate of fluid through the flowtube. A complicating factor in this measurement is that the density of typical process fluids varies. Changes in density cause the frequencies of the natural modes to vary. Since the flowmeter's control system maintains resonance, the oscillation frequency varies in response. Mass flow rate in this situation is proportional to the ratio of phase difference and oscillation frequency.

U.S. Pat. No. Re. 31,450 discloses a Coriolis flowmeter that avoids the need of measuring both phase difference and oscillation frequency. Phase difference is determined by measuring the time delay between level crossings of the two sinusoidal signals. When this method is used, the variations in the oscillation frequency cancel, and mass flow rate is proportional to the measured time delay. This measurement method is hereinafter referred to as a time delay measurement.

A problem in currently available Coriolis flow measurement apparatus is a limited suitability to gas applications. Gases are less dense than liquids and consequently, at the same flow velocities, smaller Coriolis accelerations are generated. This situation requires a higher sensitivity flowmeter. Alternatively, a flowmeter with conventional sensitivity could be used, if the flow velocity is increased to achieve the same Coriolis accelerations. Unfortunately, this alternative leads to a flowmeter having a sensitivity that is not constant.

The problems with gas flow through Coriolis flowmeters are exacerbated in systems with multiphase flow including liquids and gas. The gas damps the system with the effect of reducing sensitivity to measurement. This damping effect can be so severe that the meter cannot perform flow measurements.

Situations involving the use of Coriolis flowmeters to measure multiphase flow often arise in the petroleum industry where oil wells produce oil, gas, and water. Gas wells similarly produce gas, condensate and water. U.S. Pat. No. 5,654,502 describes a well test system where a manifold is configured to flow a selected well through a test separator, which separates the production from the well into respective portions including gas, oil or condensate, and water. A Coriolis flowmeter is used to measure the mass flow rate of the respective oil and water components. The accuracy of the flowmeter measurements is enhanced by using an electronically derived water cut measurement to correct the measured density of the segregated oil phase for residual water content. This correction process is difficult or impossible to use, in some situations, because not all wells are coupled with a test separator. It is sometimes desirable to measure the flow from a well directly and without the use or expense of a test separator. In these situations, the presence of gas in the system can be a critical limiting factor in the accuracy of measurements that are obtainable from the meter.

U.S. Pat. No. 5,029,482 teaches the use of empirically-derived correlations that are obtained by flowing combined gas and liquid flow streams having known mass percentages of the respective gas and liquid components through a Coriolis meter. The empirically-derived correlations are then used to calculate the percentage of gas and the percentage of liquid in a combined gas and liquid flow stream of unknown gas and liquid percentages based upon a direct Coriolis measurement of the total mass flow rate. The '482 patent does not address remediation of the effects of gas damping in the system measurements, though this damping effect may have an effect upon the empirical correlations.

Accordingly, there is a true need for a Coriolis flowmeter that is less sensitive to the effects of gas damping upon density measurements in multiphase flow.

SOLUTION

The present invention overcomes the problems outlined above and advances the art by providing a Coriolis flowmeter that is less sensitive to the effects of gas damping upon density measurements in multiphase flow. The meter electronics are programmed for special processing that compares drive gain against a threshold value as an indicator of multiphase flow.

The Coriolis flowmeter is broadly capable of use as a vibrating densitometer in multiphase flow environments including combinations of gas and liquids, gas and solids, or solids and liquids. The flowmeter includes at least one flowtube and a driver for vibrating the flowtube at a fundamental frequency corresponding to a density of material flowing through the flowtube. The meter electronics monitor drive gain in the vibrating flowtube for a change in value to determine the existence of multiphase flow through said flowtube. This change in value is typically a comparison against a threshold value where multiphase flow including gas and liquid is indicated by the drive gain exceeding the threshold value. A second comparison may be made against a second threshold value to indicate the existence of multiphase flow including gas and solids, liquid and solids, or liquid, gas and solids, which may exhibit similar damping effects to those of gas and liquid systems. The meter electronics respond to the existence of multiphase flow in said flowtube for the duration of the multiphase flow. This response is typically the provision of historical density data for use in determining volumetric flow rates from real time mass flow rate data from said meter. Other useful density values for use during the interval of damped multiphase flow may include density measurements obtained from selected components of the multiphase fluid.

The historical density values for use during the interval of damped multiphase flow are typically averaged over an interval of time to provide an average density value. These values may also be subjected to statistical analysis to eliminate or reduce spurious measurements from being included in the average density value. As an alternative to using historical measurement data, density values for representative fluids may be obtained from laboratory measurements or from empirically derived correlations for fluid properties including density.

The Coriolis flowmeter is intended for use in any environment where multiphase flow exists, where multiphase flow is defined as flow including at least two states of mater: solid, liquid or gas. The flowmeter is especially useful in multiphase systems including gas and liquid or gas and solids. These environments are especially common in the petroleum industry where a producing oil well or gas well can flow mist, bubbles, or other multiphase fluid systems. The flowmeter is especially useful in performing flow tests upon wells to determine the volumetric flow rates of a well as to water, gas, and oil or condensate. In these situations, the meter electronics can take action to overcome the problem of gas damping directly by increasing the backpressure on the well to force gas into solution or by indicating an alarm condition to request operator intervention.

The invention also pertains to control software including instructions for accomplishing the objectives of the invention. Specifically, the instructions are operational when executed by a processor to direct the processor to receive drive gain inputs from a Coriolis meter and process the drive gain inputs, process the drive gain inputs to determine the existence of multiphase flow through the Coriolis flowmeter by comparing the drive gain inputs against a threshold value indicative of multiphase flow, and providing outputs including a historical density value not representative of actual density measurements for the duration of the multiphase flow. These instructions are stored on a machine readable storage medium for retrieval as needed.

BRIEF DESCRIPTION OF THE DRAWINGS

FIG. 2 is a block diagram of the meter electronics in the Coriolis flowmeter;

FIG. 3 depicts a schematic diagram of a vibrating spring and weight system;

FIG. 4 depicts a schematic diagram of a vibrating spring and weight system like that of FIG., 3 but additionally including a gas damper that is analogous to gas in a multiphase flow system;

DETAILED DESCRIPTION OF THE PREFERRED EMBODIMENT

Figure 1:
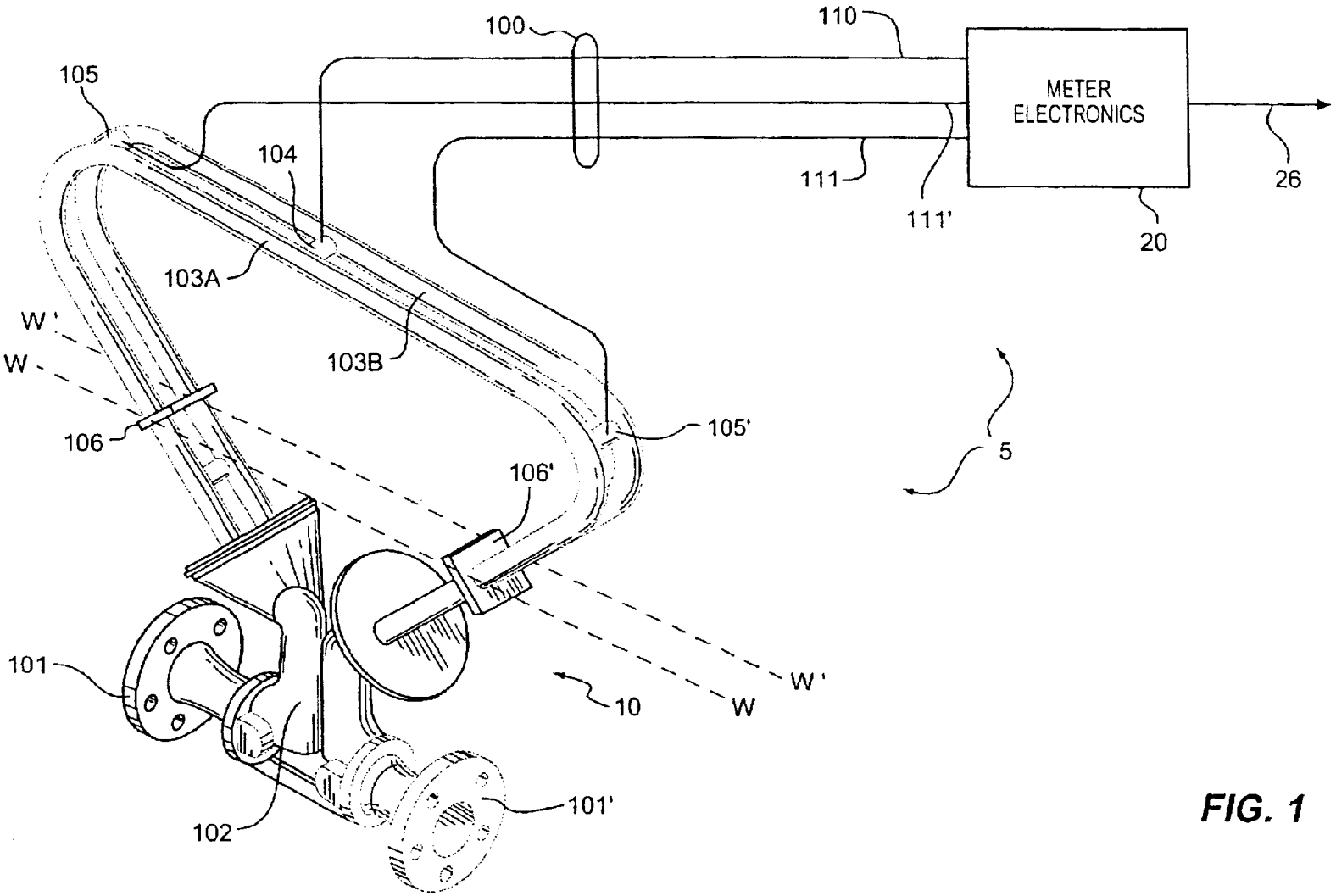
FIG. 1 depicts a Coriolis flowmeter.

Coriolis Flowmeter in General—FIG. 1

FIG. 1 illustrates a Coriolis flowmeter 5 comprising a flowmeter assembly 10 and meter electronics 20. Meter electronics 20 is connected to meter assembly 10 via leads 100 to provide density, mass flow rate, volume flow rate, totalized mass flow and other information over path 26. It should be apparent to those skilled in the art that the present invention can be used by any type of Coriolis flowmeter regardless of the number of drivers or the number of pick-off sensors.

Flowmeter assembly 10 includes a pair of flanges 101 and 101', manifold 102 and flowtubes 103A and 103B. Connected to flowtubes 103A and 103B are driver 104 and pick-off sensors 105 and 105'. Brace bars 106 and 106' serve to define the axes W and W' about which each flowtube 103A and 103B oscillates.

When flowmeter assembly 10 is inserted into a pipeline system (not shown) which carries the material being measured, material enters flowmeter assembly 10 through flange 101, passes through manifold 102 where the material is directed to enter flowtubes 103A and 103B, flows through flowtubes 103 A and 103B and back into manifold 102 where it exits meter assembly 10 through flange 101'.

Flowtubes 103A and 103B are selected and appropriately mounted to manifold 102 so as to have substantially the same mass distribution, moments of inertia, and elastic modules about bending axes W-W and W'-W' respectively. The flowtubes extend outwardly from the manifold in an essentially parallel fashion.

Flowtubes 103A-B are driven by driver 104 in opposite directions about their respective bending axes W and W' and at what is termed the first out of bending fold of the flowmeter. Driver 104 may comprise one of many well known arrangements, such as a magnet mounted to flowtube 103A and an opposing coil mounted to flowtube 103B. An alternating current is passed through the opposing coil to cause both tubes to oscillate. A suitable drive signal is applied by meter electronics 20, via lead 110 to driver 104.

The description of FIG. 1 is provided merely as an example of the operation of a Coriolis flowmeter and is not intended to limit the teaching of the present invention. The present invention is equally applicable to other types of Coriolis flowmeter including single tube meters, as well as those having multiple pickoffs or multiple drivers.

Meter electronics 20 receives the right and left velocity signals appearing on leads 11 and 111', respectively. Meter electronics 20 produces the drive signal on lead 110 causing driver 104 to oscillate flowtubes 103A and 103B. The present invention as described herein, can produce multiple drive signals from multiple drivers. Meter electronics 20 process left and right velocity signals to compute mass flow rate and provide the validation system of the present invention. Path 26 provides an input and an output means that allows meter electronics 20 to interface with an operator.

Meter Electronics 20 in General—FIG. 2

FIG. 2 illustrates a block diagram of the components of meter electronics 20 which perform the processes related to the present invention. Paths 111 and 111' transmit the left and right velocity signals from flowmeter assembly 10 to meter electronics 20. The velocity signals are received by analog to digital (A/D) convertor 203 in meter electronics 20. A/D convertor 203 converts the left and right velocity signals to digital signals usable by processor 201 and transmits the digital signals over path 213 to I/O bus 210. The digital signals are carried by I/O bus 210 to processor 201. Driver signals are transmitted over I/O bus 210 to path 212 which applies the signals to digital to analog (D/A) convertor 202. The analog signals from D/A convertor 202 are transmitted to driver 104 via path 110. Path 26 is connected to I/O bus 210 and carries signals to input and output means (not shown) which allow meter electronics 20 to receive data from and convey data to an operator.

Processor 201 reads instructions for performing the various functions of the flowmeter including but not limited to computing mass flow rate of a material, computing volume flow rate of a material, and computing density of a material from a Read Only Memory (ROM) 220 via path 221. The data as well as instructions for performing the various functions are stored in a Random Access Memory (RAM) 230. Processor 201 performs read and write operations in RAM memory 230 via path 231. In a larger sense, meter electronics 20 include additional control instrumentation and other processors that may optionally be connected to meter electronics 20 on path 26. Fluid Density Calculations FIG. 3 depicts an undamped dynamic spring assembly 300 that operates on the same physical principles as flowtubes 103A and 103B of Coriolis flowmeter 5 (see FIG. 1) in single phase flow. Spring 302 is connected to an anchor 304 and a mass 306. The mass 306 reciprocates or vibrates on a path parallel to double headed arrow 308. The natural frequency, $f_n$ of assembly 300 is:

$$f_n = \frac{1}{2\pi}\sqrt{\frac{K_s}{m}} \tag{1}$$

where $K_s$ is the spring constant of spring 302 and m is the mass of mass 306. In the case of Coriolis flowmeter 5, m is the combined weight of the flowtubes 103A and 103B together with the mass of material inside the tubes.

Where equation (1) is applied to a flowtube 103A or 103B, it becomes:

$$\rho = \frac{A}{f_n^2} - B \tag{2}$$

where A and B are calibration constants determined in a conventional manner for Coriolis flowmeters, ρ is the density of the media flowing through the flowtube, and $f_n$ is the natural frequency. Thus, by knowing the natural frequency, one can determine the density of the fluid.

Coriolis flowmeters measure mass flow rates by measuring the Coriolis twisting of a vibrating sensor tube, e.g., one of flowtubes 103A and 103B (see FIG. 1). The sensor tube vibrations have the effect of changing the angular momentum of fluid or fluids flowing inside the tube. The Coriolis twisting force is relatively small, and the flowtubes are relatively stiff. In order to make the tube vibrate with sufficient amplitude to make the Coriolis twisting force detectable, the meter electronics 20 provide a drive voltage to drive coil 104 that vibrates the flowtube or tube at its natural frequency. Thus, processor 201 (see FIG. 2) provides output that continuously maximizes the transmissivity ratio or drive gain in a conventional manner for Coriolis flowmeters. For example, the drive voltage is typically increased as the transmissivity ratio or drive gain decreases. At the same time, the drive voltage cannot be increased beyond some maximum limiting value, or else the voltage will eventually become too great with the result that the meter is damaged by excessive voltage or excessive vibration amplitudes.

The Effect of Gas Damping on the System

FIG. 4 depicts a damped dynamic spring and mass assembly 400 that operates on the same physical principles as flowtubes 103A and 103B of Coriolis flowmeter 5 (see FIG. 1) in multiphase phase flow including gas and liquid. Where possible, like numbering in FIG. 3 has been retained for identical elements in FIG. 4. FIG. 4 differs from FIG. 3 by the addition of a damper 402, which has the effect of reducing the amplitude of vibration along path 308'. Equations (1) and (2) still apply to the system shown in FIG. 4, but the overall magnitude of vibration is less due to damper 402.

Figure 5:
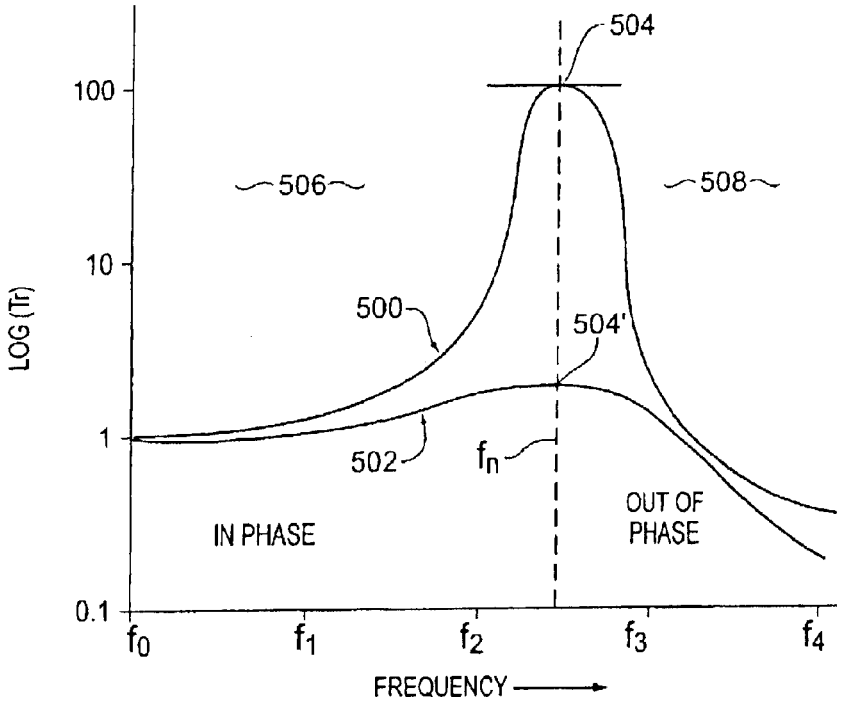
FIG. 5 depicts a plot of transmissivity versus vibrational frequency including a comparison between a hypothetical liquid system and a hypothetical liquid system that is damped by the addition of a gas component in multiphase flow.

FIG. 5 is a plot of hypothetical data demonstrating the practical effects of gas damping on the frequency response of flowtubes 103 A and 103 B in Coriolis flowmeter 5 (see also FIG. 1). The log of transmissivity is plotted as a function of the frequency of alternating voltage applied to the drive coil 104, e.g., at frequencies $f_0$, $f_1$, and $f_2$. The transmissivity ratio $T_r$ equals the pickoff output divided by the drive input, i.e., $T_r$ is the drive gain:

$$T_r = \frac{\text{OUTPUT}}{\text{INPUT}} = \frac{V_{pc}\text{PICKOFF COIL}}{V_{dc}\text{DRIVE COIL}} \tag{3}$$

where $V_{ac}$ pickoff coil is the alternating voltage on leads 111 and 111' from pickoffs 105 and 105' and $V_{ac}$ drive coil is the alternating voltage on lead 110 to drive coil 104. These voltages may be adjusted proportionally by a calibration constant to account for differences in scale between the drive coil 104 and pickoffs 105 and 105'.

A first curve 500 corresponds to the undamped system of Equation (1) and FIG. 3, i.e., no gas is present in the fluid being measured. A second curve 502 corresponds to the damped system of Equation (3). Both curves 500 and 502 have an optimal value 504 and 504', respectively, at the natural frequency $f_n$. The region 506 of curves 500 and 502 to the left of $f_n$, represents a situation where the flowtubes 103A and 103B (see FIG. 1) are vibrating in phase. The region 508 of curves 500 and 502 to the right of $f_n$ represents a situation where the flowtubes 103A and 103B (see FIG. 1) are vibrating out of phase. The optimal point 504' is more difficult to detect than optimal point 504 due to the reduced amplitude of optimal point 504'. As the amplitude decreases due to gas damping, the Coriolis flowmeter 5 (see FIG. 1) can no longer perform effective flow measurements, depending upon the sensitivity of the flowmeter.

Figure 6:
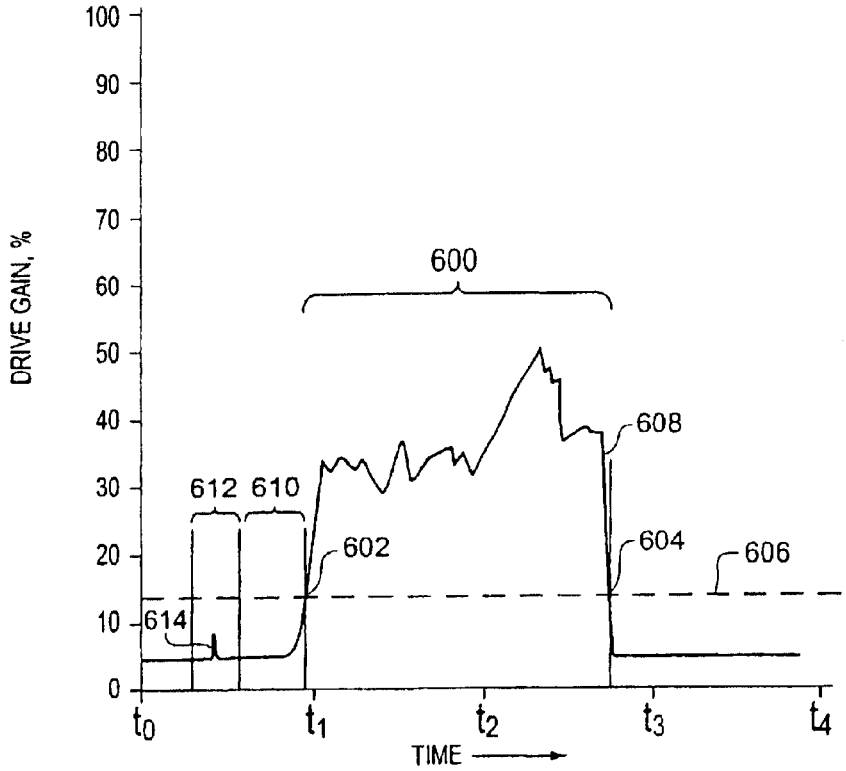
FIG. 6 depicts a plot of drive gain versus time during a transient bubble event that requires remediation.

The meter electronics 20 are designed to monitor drive gain or transmissivity and to optimize the amplitude of transmissivity based upon a ratio of the voltage at the pickoff coil divided by the voltage at the drive coil. This optimization is performed based upon a slope analysis of curve 500. For example, a first forward difference taken from new data generated by a faster frequency of vibration at the drive coil will produce a slope having a zero value (optimized condition), a negative value (region 508), or a positive value (region 506). The meter electronics then drive the vibration faster or slower, as need is indicated by the slope of the data, until an optimized transmissivity is obtained. FIG. 6 is a plot of hypothetical data showing the relationship between drive gain and time for an event 600 where a transient bubble enters a Coriolis flowmeter 5 (see FIG. 1) at time 602 and exits at time 604. Drive gain is expressed as a percent in FIG. 6, and plotted as a function of time at intervals, e.g., $t_1$, $t_2$, and $t_3$. According to the concept of the present invention, processor 201 (see also FIG. 2) is programmed with a threshold value 606 based upon drive gain or transmissivity. Where the drive gain or transmissivity of curve 608 exceeds threshold 606, processor 201 ceases to use a density value calculated in the conventional manner according to Equation (2). Processor 201 then proceeds to calculate density according to the flow chart shown ibn FIG. 7.

The effects shown in FIGS. 5–6 are similar to the effects of multiphase flow including liquids and solids, e.g., with paraffin, sand, or scale in the fluid, or with scale having actually built up on the internal flowtube walls of flowtubes 103A and 103B. Thus, a system capable of detecting gas and liquid multiphase flow is also capable of detecting, using the same principles, multiphase flow including gas and solids, liquid and solids or scale internal to the flowtubes.

Transient Bubble Remediation Mode

Figure 7:
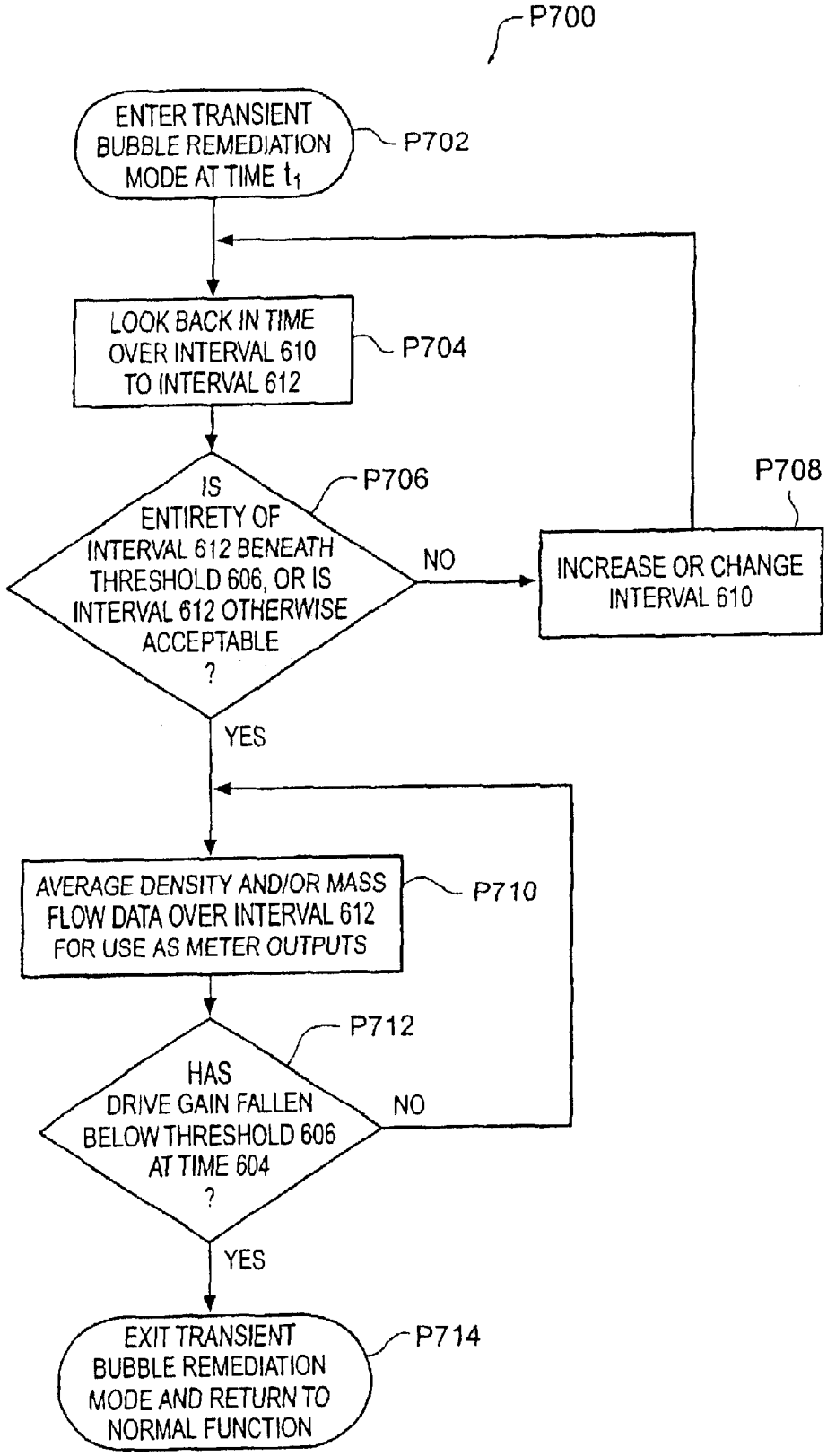
FIG. 7 depicts a schematic process control diagram demonstrating a method for remediation of the transient bubble event shown in FIG. 6.

It is always preferred to use measurements obtained according to Equation (2) for meter outputs including density values; however, it is not always possible to use Equation (2) due to the deleterious effects of gas damping in multiphase flow. FIG. 7 depicts a process P700 for remediation of density values when a transient bubble enters Coriolis flowmeter 5 with the effect of gas damping the system. Process P700 has been developed according to the premise that, while gas damping may create real-time measurement difficulties, the next best value for density obtainable from the Coriolis flowmeter is a recently measured density. The respective steps of process P700 are described in the context of reference numbers also appearing in FIG. 6.

In step P702, processor 201 determines that the drive gain has exceeded threshold 606 as a consequence of curve 608 having crossed threshold 606 at time 602. Due to the fact that the portion of curve 608 preceding time 602 may have some noise due to a bubble that is about to enter the meter, during step P704 processor 201 looks back over a predetermined time interval 610 to an averaging interval 612. Averaging interval 612 may correspond to a single data point, but it preferably comprises an interval including multiple data points for the purpose of smoothing spurious measurements 614 that may spike upwards without exceeding threshold 606.

In step P706, processor 201 determines whether any of the measurements in averaging interval 612 exceed threshold 606. If so, in step P708, a multiple or fraction of look back interval 610 may be calculated used to arrive at a new averaging interval 612 through a repetition of step P704. If repeated attempts through step P706 fail to arrive at an interval 612 having no points greater than threshold 606, then spurious measurements e.g., measurement 614, including those greater than threshold 606 can be eliminated by statistical analysis. This statistical analysis can include calculating a standard deviation and ignoring all numbers outside the standard deviation or ignoring all numbers greater than threshold 606, so long as some measurements in averaging interval 612 are less than threshold 606. Alternatively, the processor 201 can be programmed to output a preselected density value, such as may be obtained from laboratory measurements.

Step P710 includes averaging the density values over averaging interval 612 to provide an average representative density value corresponding to averaging interval 612. The values that are used to calculate this average may be adjusted by statistical analysis as discussed above in relation to step P706. In circumstances where meter diagnostics show that the flowmeter is not operating correctly to produce a mass flow rate measurement due to gas damping, the meter output for mass flow rate can also be averaged according to these same principles.

According to step P712, the processor 201 provides as a meter output the average density value obtained from step P710 until such time as curve 608 falls below threshold 606 at time 604. Accordingly, process P700 concludes at step P714 with processor 201 leaving the transient bubble remediation mode and returning to meter output consisting of measurements performed according to Equation (2).

The precise levels or durations for threshold 606, look back interval 610, and averaging interval 610 are associated with the type and size of meter, as well as the intended environment of use. For example, these values are different for meters installed on a well making one thousand barrels of oil per day versus a well making one barrel of oil. In practice, an operator determines the threshold 606 at which the Coriolis flowmeter 5 operates without bubbles. This determination is made by a combination of experience, trial and error, manufacturer's recommendations, or recording over time in the intended environment of use. The operator enters this value into the meter electronics 20 as a set value for use in process P700. The meter electronics continuously monitor the drive gain level. Applications of transient bubble remediation technology are not limited to petroleum industry applications, and include any situation where multiphase flow including gas and liquids may be encountered.

The same damping principles shown in FIG. 5 as a comparison between curves 500 and 502 apply in situations where multiphase flow includes solids and liquids, though to a lesser degree. The multiphase flow can also include a mixture of gas, liquids, and solids. In petroleum industry environments of use, these situations arise where the flow stream includes natural gas, oil or condensate, water, paraffin, sand and/or scale. Thus, the principles of FIGS. 6 and 7 may be used to remediate erroneous density or mass flow rate measurements due to multiphase flow including solids and liquids or gas and solids, as well as gas and liquids.

The above-described process elements are comprised of instructions that are stored on storage media. The instructions can be retrieved and executed by a processor. Some examples of instructions are software, program code, and firmware. Some examples of storage media are memory devices, tape, disks, integrated circuits, and servers. The instructions are operational when executed by the processor to direct the processor to operate in accord with the invention. The term "processor" refers to a single processing device or a group of inter-operational processing devices. Some examples of processors are integrated circuits, computers, and logic circuitry. Those skilled in the art are familiar with instructions, processors, and storage media.

Coriolis flowmeters and associated meter electronics that are equipped to implement the principles of transient bubble remediation discussed above can be used in any environment containing multiphase flow, and the meters work especially well to remediate transient mist and fine bubbles. In this context, "transient" means a flow condition that exists temporarily or periodically over time. The meters also work acceptably well to remediate gas effects in slug flow or plug flow conditions, although, the calculated volumetric flow rates are less reliable under these flow conditions than for mist flow conditions. Specific applications include chemical processes with gas genesis in a reactor or process flow line, retort processing of foods, microbiological processes with gas genesis, and any other system with multiphase fluids, such as producing wells in the petroleum industry where a separator has not been installed prior to the meter.

A System For Use in Petroleum Well Test Measurements

Figure 8:
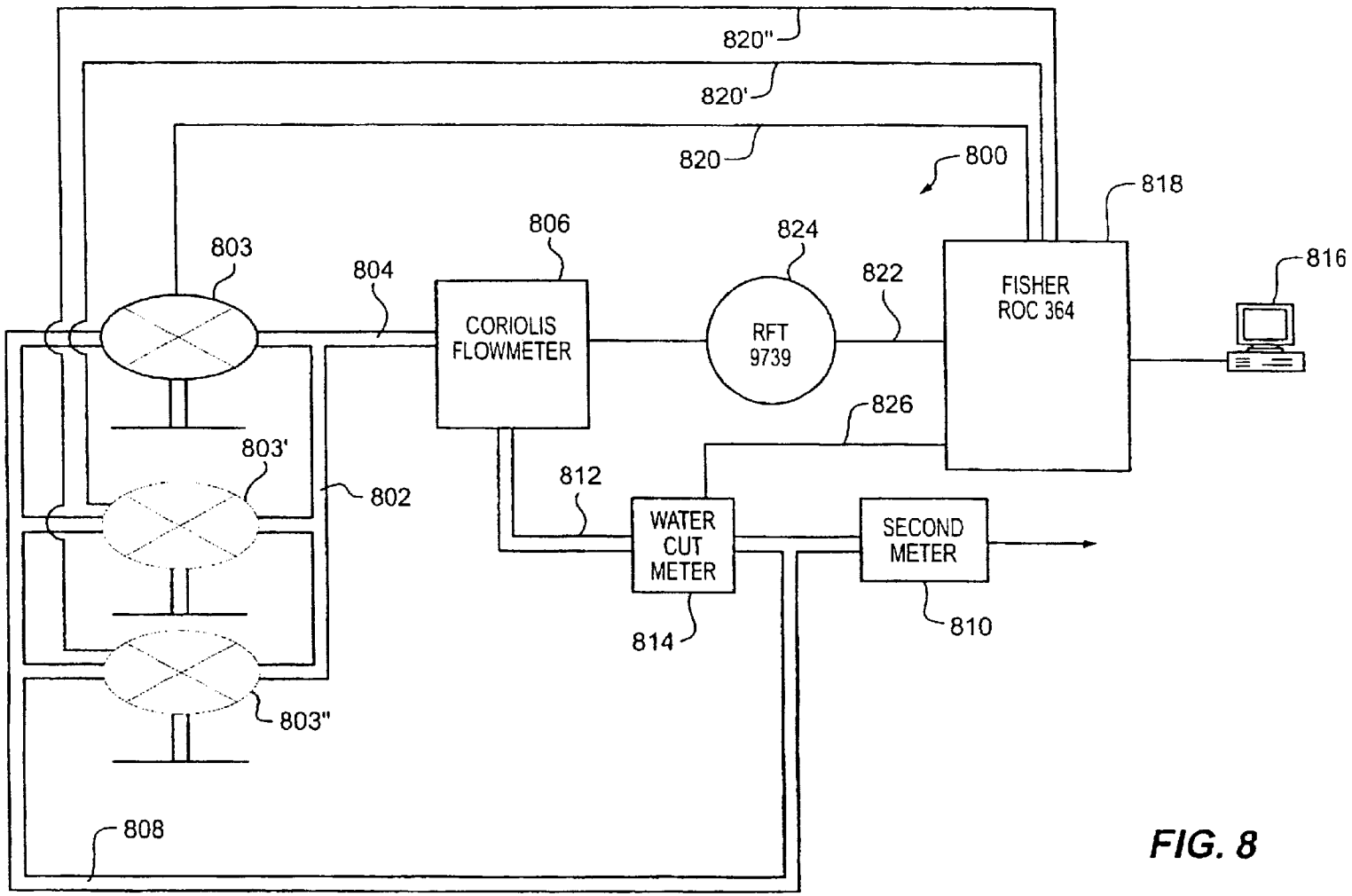
FIG. 8 depicts a schematic block diagram of a well test system incorporating control circuitry capable of implementing the method shown in FIG. 7.

As shown in FIG. 8, a schematic block diagram, system 800 includes a manifold 802 having a plurality of electronically actuated wellhead valves 803, 803', and 803" that each provide multiphase flow including gas, liquid and solids to tubing 804. Valves 803, 803' and 803" are preferably three-way electronically-initiated, pneumatically actuated valve, such as the Xomox TUFFLINE037AX WCB/316 well switching valve with a MATRYX MX 200 actuator. Valves 803, 803' and 803" are selectively configured to provide multiphase flow from one well at a time through manifold 802 and tubing 804 to Coriolis flowmeter 806, which may be the same as Coriolis flowmeter 5. Coriolis flowmeter 806 measures the volumetric flow rate of one of the wells connected to valves 803, 803', or 803". The volumetric flow rate of the well helps to determine the contribution of this particular well to total sales. The remainder of material from the other wells connected to valves 803, 803', and 803" flow through the line 808 for passage through second meter 810, which may be a sales meter. Flow through Coriolis flowmeter 806 discharges into meter discharge line 812 and enters water cut meter 812. The flow is thereafter combined with the flow in gathering line 808 for measurement through second meter 810. Exemplary forms of flowmeters 806 and 810 include the ELITE Models CMF 300356NU and Model CMF300H551NU, which are available from Micro Motion of Boulder, Colo.

System 800 includes a computer 816 (e.g., an IBM compatible machine) that is programmed with data acquisition and programming software. A preferred form of this software is the Intellution software DMACS, which is available from INTELLUTION, a subsidiary of Emerson Electric. This software is particularly preferred because it can generate alarms that indicate abnormal well test conditions representative of mechanical failures which are potentially dangerous. Computer 816 controls the programming of remote operations controller 818, which includes a plurality of drivers and interfaces that permit computer 816 to interact with remote components of system 800. A preferred form of remote operations controller 818 is the Fisher Model ROC364. Controller 818 may also be programmed with software to facilitate the implementation of control instructions from computer 816.

Valve control leads 820, 820' and 820" connect controller 818 with the [Lead 822 connects controller 818 with pressure transmitter 824] *electrically actuated valves 803, 803', and 803" for selective control of the valves*. An exemplary form of transmitter 824 is the ELITE Model RFT9739, which is available from Micro Motion of Boulder, Colo. Lead 826 connects controller 818 with water-cut meter 814. The functions of controller 818, transmitter 824, and computer 816 may be combined in a single processor, such as processor 201 of meter electronics 20 (see FIG. 2).

System 800 operates as follows. Manifold 802 carries a material from single valve 803, 803', or 803" to flow through Coriolis flowmeter 806 to test a well or provide mass flow rate information concerning a well connected to the single valve 803, 803', or 803". The material flowing through the remaining valves 803, 803', or 803" flow into gathering line 808 for combined sales output through second meter 810. Coriolis flowmeter 806 provides density and mass flow rate information as meter outputs to transmitter 824 which, in turn, provides signals to controller 818 on lead 822. One of computer 816, controller 818, transmitter 824 or Coriolis flowmeter 806 (typically computer 816 ) performs a calculation for total volumetric flow rate $Q_e$ according to Equation (4):

$$Q_r = \frac{M_c}{D_c} \tag{4}$$

wherein $M_e$ is a Coriolis-based mass flow rate measurement obtained from the total combined oil and water flow stream; and $D_e$ is a density of the total combined oil, gas, water and solids flow stream at a measurement temperature T.

A volumetric flow rate of oil is calculated according to Equation (5):

$$Q_o = Q_e(1 - X_w) \tag{5}$$

wherein $Q_o$ is a volumetric flow rate of oil; $X_W$ is the fractional flow rate of water, and the remaining variables are defined above.

A volumetric flow rate of water is calculated according to Equation (6):

$$Q_w = Q_e * X_w \tag{6}$$

wherein $Q_w$ is a volumetric flow rate of water, and the remaining variables are defined above.

The volumetric flow rate values $Q_o$ and $Q_w$ can be corrected to a standard reference temperature, $T_{ref}$, through multiplication of the volumetric flow rate values by the density at a measurement temperature and dividing by the density at the reference temperature, e.g., as in Equation (7):

$$Q_w = Q_{o.T} = \frac{D_{0.T}}{D_0} \tag{7}$$

wherein $Q_o$ is a volumetric oil flow rate at a standard reference temperature $T_{ref}$; $Q_{o,T}$ is a volumetric oil flow rate measured at temperature T and calculated according to Equation (5); Do is a measured density of oil from laboratory measurements at reference temperature $T_{ref}$; and $D_{o,T}$ is a density of oil measured at temperature T.

The fractional flow rate of water is calculated as:

$$X_w = \frac{D_c - \rho_{o.t}}{\rho_{w.T} - \rho_{o.T}} \tag{8}$$

wherein $D_e$ is a density of the total combined oil (or condensate) and water flow stream at a measurement temperature T. $\rho_{o,T}$ is a density of the pure oil (or condensate) phase excluding any residual water content of the segregated oil component; $\rho_{W,T}$ is a density of the pure water phase; and the remaining variables are defined above.

The value $X_W$ is a 'water-cut' measurement, which is an important result of well test measurements. The term 'water-cut' is hereby defined as any ratio that represents a relationship between a volume of oil and a volume of water in an oil and water liquid mixture. Water-cut meter 814 uses capacitance, resistance, microwave radiation or other measurements to quantify the water-cut. In some circumstances, the volume of water is so great that it exceeds the limits of the instrumentation. For example, capacitance or resistance monitors provide acceptably accurate water-cut measurements only where the water volume is less than about 20% to 30% of the total flow stream. The upper 30% accuracy limit is far below the level that is observed from many producing wells. For example, the total liquid production volume of an oil well can be 99% water. Some water-cut monitors, therefore, are relegated to determining the water-cut in an oil component that has a low water content. Water-cut monitors most often cannot be used to determine the water content in the material that flows from a two phase separator because the total liquid component has a water content that exceeds the 30% upper accuracy limit. An exemplary form of water cut monitor 66 is the Drexelbrook Model CM-2 capacitance monitor. Accordingly, Equation (8) provides a method for calculating water cut and the volumetric flow rate of water and oil or condensate. The values $\rho_{o,T}$ and $\rho_{w,T}$ can be obtained from conventional laboratory measurements of produced fluids from a particular well.

Where the value $X_W$ is within the performance and accuracy limits of water cut meter 814, the oil density may be corrected for water content as follows:

$$\rho_{o,t} = \frac{\rho_t - \rho_{w,T}\mathrm{WC}}{1 - \mathrm{WC}} \tag{9}$$

wherein $\rho_{o,T}$ is water-corrected oil density at temperature T; $\rho_t$ is the total density of the combined water-cut liquid as measured by the Coriolis flowmeter 806 at temperature T; $\rho_w$ is the density of the water component established by laboratory measurement or a conventional empirical temperature-salinity correlation at temperature T; and WC is the water-cut measured by the water-cut monitor 814.

In summary, it is necessary to convert meter liquid measurements from mass flow rates into volumetric flow rates for sales purposes because petroleum products are sold by volume. Density values are used to perform the conversion from mass flow rate into a volumetric flow rate. The fractional flow rates of water and oil are determinable by direct measurement of water cut, but this method does not always work due to instrumentation constraints inherent to water cut meters. The direct measurement of water cut can also be used to calibrate the meter for a changing oil density value over the life of a producing well. Water cut is determinable from the density measurement if the respective densities of water and oil are known from other sources. Gas damping on the system interferes with these calculations according to Equations (8) and (9) because damping may be so severe that the the meter ceases to provide accurate density readings of material flowing through the flowtubes or because the measured density represents a sufficient gas content to destroy the assumption of two phase flow that is inherent to Equations (8) and (9). The rate of gas flow can be determined by empirical correlations according to U.S. Pat. No. 5,029,482, which is hereby incorporated by reference to the same extent as though fully disclosed herein.

It follows that computer 816 or controller 818 of FIG. 8 have the option of processing using a density or mass flow rate value obtained according to FIG. 7 while a transient bubble is detected within flowmeter 806. Alternatively, if use of the average value from interval 612 is not desired, alternative options include stopping the well test or indicating an alarm for operator intervention. Yet another option is for computer 816 to signal controller 818 to partially close the selected one of valves 803, 803' or 803" to increase the back-pressure on the well. In the case of an oil well, this backpressure may force liberated gas back into solution, thereby completely or partially overcoming the effects of gas damping on Coriolis flowmeter 806 by the total or partial elimination of gas from the production fluid.

Equations (8) and (9) specifically refer to oil and water, but the equations more broadly refer to any dual phase immiscible liquid system, e.g., any colloidal solution, that may also be affected by gas as a third phase. The deleterious effects of gas upon these systems includes more than mere damping because $X_W$ values calculated using the density from equation (8), as corrected by Equation (9), has error due to the reduced density value $D_e$ when the equations were developed on the assumption of dual phase immiscible liquids without taking gas into consideration.

Those skilled in the art will understand that the preferred embodiments described above may be subjected to apparent modifications without departing from the true scope and spirit of the invention. The inventor, accordingly, hereby states his intention to rely upon the Doctrine of Equivalents, in order to protect his full rights in the invention.

What is claimed is:

1. A Coriolis flowmeter which measures densities of materials including combinations of gas and liquids, gas and solids, or solids and liquids, said flowmeter comprising:

at least one flowtube;

a driver that vibrates said at least one flowtube at a fundamental frequency based on a drive signal, said fundamental frequency corresponding to a density of material flowing through said at least one flowtube;

pickoffs affixed to said at least one flowtube that generate pickoff signals responsive to said material flowing through said at least one flowtube; and meter electronics configured to:

determine said density of said material flowing through said at least one flowtube based on at least one of said pickoff signals, monitor a drive gain in said at least one flow tube for a change in value to determine if said material flowing through said at least one flowtube comprises a multiphase flow, and if said material flowing through said at least one flowtube comprises a multiphase flow, then determine said density of said material flowing through said at least one flowtube based on a stored density value.

2. The flowmeter as set forth in claim 1 wherein said meter electronics is further configured to determine whether said drive gain exceeds a first threshold value to determine if said material flowing through said at least one flowtube comprises said multiphase flow.

3. The flowmeter as set forth in claim 2 wherein said first threshold value represents said multiphase flow includes gas and liquids.

4. The flowmeter as set forth in claim 3 wherein said meter electronics is further configured to determine whether said drive gain exceeds a second threshold value, said second threshold value represents that said multiphase flow includes liquid and solid matter.

5. The flowmeter as set forth in claim 1 wherein said meter electronics is further configured to average historical density measurements over an interval of time to determine said density if said material flowing through said at least one flowtube comprises said multiphase flow.

6. The flowmeter as set forth in claim 5 wherein said meter electronics is further configured to apply a statistical analysis to said historical density measurements to eliminate or reduce spurious measurements.

7. The flowmeter as set forth in claim 1 wherein said meter electronics is further configured to process density measurements obtained from laboratory measurements to determine said density if said material flowing through said at least one flowtube comprises said multiphase flow.

8. The flowmeter as set forth in claim 1 wherein said meter electronics is further configured to process correlations to determine said density if said material flowing through said at least one flowtube comprises said multiphase flow.

9. The flowmeter as set forth in claim 1 further comprising:

circuitry configured to close a valve to stop a well test in progress on a fluid flowing from a production well.

10. The flowmeter as set forth in claim 1 further comprising:

means for indicating an alarm indicative of said multiphase flow.

11. A method of operating a Coriolis flowmeter to measure densities of materials, said method comprising the steps of:

vibrating at least one flowtube of said Coriolis flowmeter at a fundamental frequency corresponding to a density of material flowing through said at least one flowtube;

generating pickoff signals that represent motion of said at least one flow tube as said material flows through said at least one flowtube;

determining said density of said material flowing through said at least one flowtube based on at least one of said pickoff signals;

monitoring a drive gain in said at least one flowtube for a change in value to determine if said material flowing through said at least one flowtube comprises a multiphase flow; and if said material flowing through said at least one flowtube comprises said multiphase flow, then determining said density of said material flowing through said at least one flowtube based on a stored density value.

12. The method as set forth in claim 11 wherein said step of monitoring said drive gain includes comparing said drive gain to a first threshold value to determine if said drive gain exceeds said first threshold value to determine if said material flowing through said at least one flowtube comprises said multiphase flow.

13. The method as set forth in claim 12 wherein said step of comparing includes setting said first threshold value to represent that said multiphase flow includes gas and liquids.

14. The method as set forth in claim 11 wherein said step of comparing includes setting a second threshold value to represent that said multiphase flow includes liquids and solid matter and comparing said drive gain to said second threshold value to determine whether said drive gain exceeds said second threshold value.

15. The method as set forth in claim 11 wherein said step of determining said density of said material flowing through said at least one flowtube based on said stored density value further includes a step of averaging historical density measurements over an interval of time to determine said density.

16. The method as set forth in claim 15 wherein said step of averaging said historical density measurements further includes a step of applying a statistical analysis to said historical density measurements to eliminate or reduce spurious measurements.

17. The method as set forth in claim 11 wherein said *step* of determining said density of said material flowing through said at least one flowtube based on said stored density value further includes processing density measurements obtained from laboratory measurements to determine said density.

18. The method as set forth in claim 11 wherein said step of determining said density of said material flowing through said at least one flowtube based on said stored density value further includes processing correlations to determine said density.

*19. A Coriolis flowmeter which measures mass flow rates of materials including combinations of gas and liquids, gas and solids, or solids and liquids, said flowmeter comprising:*

*at least one flowtube;*

*a driver that vibrates said at least one flowtube at a fundamental frequency based on a drive signal;*

*pickoffs affixed to said at least one flowtube that generate pickoff signals responsive to said material flowing through said at least one flowtube; and*

*meter electronics configured to:*

*determine said mass flow rate of said material flowing through said at least one flowtube based on said pickoff signals,*

*monitor a drive gain in said at least one flow tube for a change in value to determine if said material flowing through said at least one flowtube comprises a multiphase flow, and*

*if said material flowing through said at least one flowtube comprises a multiphase flow, then determine said mass flow rate of said material flowing through said at least one flowtube based on a stored mass flow rate value.*

*20. The flowmeter as set forth in claim 19 wherein said meter electronics is further configured to determine whether said drive gain exceeds a first threshold value to determine if said material flowing through said at least one flowtube comprises said multiphase flow.*

*21. The flowmeter as set forth in claim 20 wherein said first threshold value represents that said multiphase flow includes gas and liquids.*

*22. The flowmeter as set forth in claim 21 wherein said meter electronics is further configured to determine whether said drive gain exceeds a second threshold value, said second threshold value represents that said multiphase flow includes liquid and solid matter.*

*23. The flowmeter as set forth in claim 19 wherein said meter electronics is further configured to average historical mass flow rate measurements over an interval of time to determine said mass flow rate if said material flowing through said at least one flowtube comprises said multiphase flow.*

*24. The flowmeter as set forth in claim 23 wherein said meter electronics is further configured to apply a statistical analysis to said historical mass flow rate measurements to eliminate or reduce spurious measurements.*

*25. The flowmeter as set forth in claim 19 wherein said meter electronics is further configured to process correlations to determine said mass flow rate if said material flowing through said at least one flowtube comprises said multiphase flow.*

*26. The flowmeter as set forth in claim 19 further comprising:*

*circuitry configured to close a valve to stop a well test in progress on a fluid flowing from a production well.*

*27. The flowmeter as set forth in claim 19 further comprising:*

*means for indicating an alarm indicative of said multiphase flow.*

*28. A method of operating a Coriolis flowmeter to measure mass flow rates of materials, said method comprising the steps of:*

*vibrating at least one flowtube of said Coriolis flowmeter at a fundamental frequency corresponding to a mass flow rate of material flowing through said at least one flowtube;*

*generating pickoff signals that represent motion of said at least one flow tube as said material flows through said at least one flowtube;*

*determining said mass flow rate of said material flowing through said at least one flowtube based on said pickoff signals;*

*monitoring a drive gain in said at least one flowtube for a change in value to determine if said material flowing through said at least one flowtube comprises a multiphase flow; and*

*if said material flowing through said at least one flowtube comprises said multiphase flow, then determining said mass flow rate of said material flowing through said at least one flowtube based on a stored mass flow rate value.*

*29. The method as set forth in claim 28 wherein said step of monitoring said drive gain includes comparing said drive gain to a first threshold value to determine if said drive gain exceeds said first threshold value to determine if said material flowing through said at least one flowtube comprises said multiphase flow.*

*30. The method as set forth in claim 29 wherein said step of comparing includes setting said first threshold value to represent that said multiphase flow includes gas and liquids.*

*31. The method as set forth in claim 28 wherein said step of comparing includes setting a second threshold value to represent that said multiphase flow includes liquids and solid matter and comparing said drive gain to said second threshold value to determine whether said drive gain exceeds said second threshold value.*

*32. The method as set forth in claim 28 wherein said step of determining said mass flow rate of said material flowing through said at least one flowtube based on said stored mass flow rate value further includes a step of averaging historical mass flow rate measurements over an interval of time to determine said mass flow rate.*

*33. The method as set forth in claim 32 wherein said step of averaging said historical mass flow rate measurements further includes a step of applying a statistical analysis to said historical mass flow rate measurements to eliminate or reduce spurious measurements.*

*34. The method as set forth in claim 28 wherein said step of determining said mass flow rate of said material flowing through said at least one flowtube based on said stored mass flow rate value further includes processing correlations to determine said mass flow rate.*

*35. A flowmeter, comprising:*

*at least one flowtube;*

*a driver that vibrates said at least one flowtube based on a drive signal;*

*pickoffs affixed to said at least one flowtube that generate pickoff signals comprising a vibrational response to said material flowing through said at least one flowtube; and*

*meter electronics configured to:*

*monitor said vibrational response for a change in value to determine if said material flowing through said at least one flowtube comprises a multiphase flow; and*

*substitute remediation data in place of a flowmeter measurement if said material flowing through said at least one flowtube comprises said multiphase flow.*

*36. The flowmeter of claim 35, with said flowmeter comprising a Coriolis flowmeter.*

*37. The flowmeter of claim 35, with said flowmeter comprising a vibrating densitometer.*

*38. The flowmeter of claim 35, with said vibrational response comprising a pickoff frequency to drive frequency ratio.*

*39. The flowmeter of claim 35, with said vibrational response comprising a drive gain.*

*40. The flowmeter of claim 35, with said monitoring further comprising:*

*comparing said vibrational response to a first threshold value; and*

*determining that said material flowing through said at least one flowtube comprises said multiphase flow if said vibrational response exceeds said first threshold value.*

*41. The flowmeter of claim 35, with said monitoring further comprising:*

*comparing said vibrational response to a second threshold value; and*

*determining that said multiphase flow includes liquids and solid matter if said vibrational response exceeds said second threshold value.*

*42. The flowmeter of claim 35, with said remediation data comprising historical data.*

*43. The flowmeter of claim 35, with said remediation data comprising averaged historical data.*

*44. The flowmeter of claim 35, with said remediation data comprising historical data wherein spurious measurement values have been substantially eliminated.*

*45. The flowmeter of claim 35, with said remediation data comprising empirical measurement data.*

*46. The flowmeter of claim 35, with said remediation data comprising measurement data received from an outside density meter.*

*47. The flowmeter of claim 35, with said remediation data comprising previous measurement data.*

*48. The flowmeter of claim 35, with said remediation data comprising previous measurement data and with the method further comprising:*

*comparing said vibrational response to a multiphase threshold value;*

*determining that said material flowing through said at least one flowtube comprises said multiphase flow if said vibrational response exceeds said multiphase threshold value;*

*testing measurements of a previous measurement interval for flowmeter measurements above said multiphase threshold value; and*

*using said measurements of said previous measurement interval as said remediation data if said measurements of said previous measurement interval do not exceed said multiphase threshold value.*

*49. The flowmeter of claim 35, further comprising generating an alarm if said material flowing through said at least one flowtube comprises said multiphase flow.*

*50. The flowmeter of claim 35, further comprising increasing a back pressure in a connected flow conduit if said material flowing through said at least one flowtube comprises said multiphase flow.*

*51. The flowmeter of claim 35, further comprising stopping said material from flow if said material flowing through said at least one flowtube comprises said multiphase flow.*

*52. The flowmeter of claim 35, further comprising generating flow measurements for one or more selected flow components of the multiphase flow if said material flowing through said at least one flowtube comprises said multiphase flow.*

*53. A method of operating a flowmeter, comprising:*

*vibrating at least one flowtube of said flowmeter based on a drive signal;*

*monitoring a vibrational response in said at least one flowtube for a change in value to determine if said material flowing through said at least one flowtube comprises a multiphase flow; and*

*substituting remediation data in place of a flowmeter measurement if said material flowing through said at least one flowtube comprises said multiphase flow.*

*54. The method of claim 53, with said flowmeter comprising a Coriolis flowmeter.*

*55. The method of claim 53, with said flowmeter comprising a vibrating densitometer.*

*56. The method of claim 53, with said vibrational response comprising a pickoff frequency to drive frequency ratio.*

*57. The method of claim 53, with said vibrational response comprising a drive gain.*

*58. The method of claim 53, with said monitoring further comprising:*

*comparing said vibrational response to a first threshold value; and*

*determining that said material flowing through said at least one flowtube comprises said multiphase flow if said vibrational response exceeds said first threshold value.*

*59. The method of claim 53, with said monitoring further comprising:*

*comparing said vibrational response to a second threshold value; and*

*determining that said multiphase flow includes liquids and solid matter if said vibrational response exceeds said second threshold value.*

*60. The method of claim 53, with said remediation data comprising historical data.*

*61. The method of claim 53, with said remediation data comprising averaged historical data.*

*62. The method of claim 53, with said remediation data comprising historical data wherein spurious measurement values have been substantially eliminated.*

*63. The method of claim 53, with said remediation data comprising empirical measurement data.*

*64. The method of claim 53, with said remediation data comprising measurement data received from an outside density meter.*

*65. The method of claim 53, with said remediation data comprising previous measurement data.*

*66. The method of claim 53, with said remediation data comprising previous measurement data and with the method further comprising:*

*comparing said vibrational response to a multiphase threshold value;*

*determining that said material flowing through said at least one flowtube comprises said multiphase flow if said vibrational response exceeds said multiphase threshold value;*

*testing measurements of a previous measurement interval for flowmeter measurements above said multiphase threshold value; and*

*using said measurements of said previous measurement interval as said remediation data if said measurements of said previous measurement interval do not exceed said multiphase threshold value.*

*67. The method of claim 53, further comprising generating an alarm if said material flowing through said at least one flowtube comprises said multiphase flow.*

*68. The method of claim 53, further comprising increasing a back pressure in a connected flow conduit if said material flowing through said at least one flowtube comprises said multiphase flow.*

*69. The method of claim 53, further comprising stopping said material from flow if said material flowing through said at least one flowtube comprises said multiphase flow.*

*70. The method of claim 53, further comprising generating flow measurements for one or more selected flow components of the multiphase flow if said material flowing through said at least one flowtube comprises said multiphase flow.*

* * * * *

UNITED STATES PATENT AND TRADEMARK OFFICE

CERTIFICATE OF CORRECTION

PATENT NO. : RE 40,095 E
APPLICATION NO. : 10/430879
DATED : February 26, 2008
INVENTOR(S) : Robert E. Dutton It is certified that error appears in the above-identified patent and that said Letters Patent is hereby corrected as shown below:

Column 6, equation (3) should appear as follows:

$$T_r = \frac{OUTPUT}{INPUT} = \frac{V_{ac}PICKOFF \quad COIL}{V_{ac}DRIVE \quad COIL}$$

Column 9, line 29, replace "through the line 808" with -- through to line 808 --

Column 10, equation (4) should appear as follows:

$$Q_e = \frac{M_e}{D_e}$$

Column 10, equation (7) should appear as follows:

$$Q_o = Q_{o.T} = \frac{D_{O.T}}{D_O}$$

Column 10, equation (8) should appear as follows:

$$X_w = \frac{D_e - \rho_{O.T}}{\rho_{w.T} - \rho_{O.T}}$$

Column 11, equation (9) should appear as follows:

$$\rho_{o.T} = \frac{\rho_t - \rho_{w.t}WC}{1 - WC}$$

Signed and Sealed this

First Day of June, 2010

David J. Kappos

David J. Kappos
*Director of the United States Patent and Trademark Office*